United States Patent [19]

Davis

[11] Patent Number: 5,074,854
[45] Date of Patent: Dec. 24, 1991

[54] DISPOSABLE UNDERGARMENT HAVING A BREAK-AWAY PANEL

[75] Inventor: Karen M. Davis, Cincinnati, Ohio

[73] Assignee: The Procter & Gamble Co., Cincinnati, Ohio

[21] Appl. No.: 572,660

[22] Filed: Aug. 24, 1990

[51] Int. Cl.⁵ .................... A61F 13/20; A61F 13/15
[52] U.S. Cl. ......................... 604/385.1; 604/385.2; 604/396
[58] Field of Search .............. 604/358, 385.1, 385.2, 604/396, 367, 368; 2/70, 73, 75, 78 R, 78 B, 400–408, 209.4, 209.5, 209.7, 228, 238, DIG. 1

[56] References Cited

U.S. PATENT DOCUMENTS

| | | | |
|---|---|---|---|
| Re. 32,649 | 4/1988 | Brandt et al. | 604/368 |
| 1,571,016 | 1/1926 | Lesser | 2/DIG. 1 X |
| 2,397,751 | 4/1946 | Rand | 2/DIG. 1 X |
| 3,150,665 | 9/1964 | May, Jr. et al. | 2/DIG. 1 X |
| 3,207,625 | 3/1966 | Johnson | 128/288 |
| 3,329,145 | 7/1967 | Merre | 604/368 |
| 3,761,962 | 10/1973 | Myers | 2/DIG. 1 X |
| 3,971,379 | 7/1976 | Chatterjee | 604/368 |
| 4,122,552 | 10/1978 | Tedford | 2/78 R |
| 4,126,903 | 11/1978 | Horton | 2/DIG. 1 X |
| 4,145,763 | 3/1979 | Abrams et al. | 2/403 |
| 4,205,679 | 6/1980 | Repke et al. | 128/287 |
| 4,435,178 | 3/1984 | Fitzgerald | 604/368 |
| 4,515,595 | 5/1985 | Kievit et al. | 604/385 A |
| 4,610,678 | 9/1986 | Weisman et al. | 604/368 |
| 4,610,680 | 9/1986 | LaFleur | 604/385 |
| 4,610,681 | 9/1986 | Strohbeen et al. | 604/396 |
| 4,619,649 | 10/1986 | Roberts | 604/396 |
| 4,630,320 | 12/1986 | Van Gompel | 2/406 |
| 4,641,381 | 2/1987 | Heran et al. | 2/400 |
| 4,646,362 | 3/1987 | Heran et al. | 2/400 |
| 4,673,402 | 6/1987 | Weisman et al. | 604/368 |
| 4,690,681 | 9/1987 | Haunschild et al. | 604/396 |
| 4,743,239 | 5/1988 | Cole | 604/385 |
| 4,745,636 | 5/1988 | Lunt | 2/403 X |
| 4,747,846 | 5/1988 | Boland et al. | 604/38 A |
| 4,834,735 | 5/1989 | Alemany et al. | 604/368 |
| 4,843,654 | 7/1989 | Marca | 2/228 X |
| 4,850,056 | 7/1989 | Gardner et al. | 2/DIG. 4 X |
| 4,909,804 | 3/1990 | Douglas, Sr. | 604/385.2 |
| 4,923,454 | 5/1990 | Seymour et al. | 604/368 |
| 4,938,753 | 7/1990 | Van Gompel et al. | 604/385.2 |
| 4,938,757 | 7/1990 | Van Gompel et al. | 604/396 |
| 4,940,463 | 7/1990 | Leathers et al. | 604/396 |
| 4,940,464 | 7/1990 | Van Gompel et al. | 604/396 |
| 4,944,733 | 7/1990 | Casale | 604/385.1 |
| 4,972,525 | 11/1990 | Hwang | 2/403 X |

*Primary Examiner*—David J. Isabella
*Assistant Examiner*—Elizabeth M. Burke
*Attorney, Agent, or Firm*—Steven W. Miller; T. H. O'Flaherty; R. C. Witte

[57] ABSTRACT

A disposable undergarment having at least one break-away panel comprised of one or more strips of manually tearable material uninterruptedly extending from one leg opening to the waist opening which allows the disposable undergarment to be torn open and removed without sliding the undergarment down the length of both legs.

29 Claims, 2 Drawing Sheets

DISPOSABLE UNDERGARMENT HAVING A BREAK-AWAY PANEL

FIELD OF THE INVENTION

The present invention relates to disposable undergarments such as disposable training pants, incontinent briefs and the like, and more particularly, disposable undergarments which can be quickly opened to facilitate removal from the user.

BACKGROUND OF THE INVENTION

With regard to disposable undergarments and in particular with regard to disposable training pants, which are put on by placing the user's feet in the leg openings and sliding the training pants up the legs into position, it is desirable to have a means for opening the training pants so the training pants can be easily removed. This becomes especially important when the training pants are soiled and the soilage could be spread and smeared if the training pants had to be removed by sliding them down the length of one or both legs.

The need for disposable training pants to be openable is well known, and various means of accomplishing this are also known. Additionally, it is known in the art that it is desirable to have a product which is very garment-like in its appearance and feel, so a child will distinguish it from a diaper, and will easily adjust to cloth undergarments.

Most disposable training pants are made openable by providing side seams which are separable. Most of these separable seams are sealed using thermal, ultrasonic, pressure, or adhesive bonding. Despite the effectiveness of this means of making the disposable training pants openable, it requires a seam with a dual function, i.e., the seam has to be strong enough to hold the pants together, yet the seam must also be weak enough to be separable. These types of seams, also, do not provide the desired garment-like appearance unless an inwardly facing seam is provided, but such inwardly facing seams tend to rub and irritate the skin of the wearer.

Other known methods to make disposable training pants openable, are the use of perforations or scoring to weaken the sides of the training pants or the use of chain stitching at the seams which allows the seams to unravel by pulling on a loose thread. However, most disposable training pants are made using thin, nonwoven materials. It is difficult to control the strength of thin, nonwoven materials with perforations or scoring. And, although chain stitching provides a very garment-like appearance, it often results in premature unraveling and separation of the seam, or alternatively it is inconvenient to find and get a hold of the loose thread to unravel the seam.

Therefore, it is an object of the present invention to provide a disposable undergarment with an improved means of opening the undergarment to facilitate removal from the user.

It is also an object of the present invention to provide a disposable undergarment which has a region on at least one side of the undergarment which is substantially free from extra mass such as absorbent material or elastic legbands or waistbands, and can be easily torn without the use of perforations or scoring.

It is a further object of the present invention to provide a disposable undergarment having seams which are firmly secured without affecting the disposable undergarment's ability to be opened.

It is a still further object of the present invention to provide a disposable undergarment which will have a garment-like appearance and feel.

It is a still further object of the present invention to provide a disposable undergarment with an improved means of controlling the disposable undergarment's strength and ability to open.

It is a still further object of the present invention to provide a disposable undergarment with an improved means of opening which will allow the disposable undergarment to be constructed of a wider range of materials.

SUMMARY OF THE INVENTION

In accordance with the present invention, a disposable undergarment is provided with a break-away panel to enhance the ease with which the undergarment is removed, allow the seams to be made more securely, and allow more versatility in the manufacture of the disposable undergarment. The disposable undergarment generally comprises a front portion, a rear portion, o and crotch portion secured to form a waist opening and two leg openings, and is substantially comprised of a material which is suitable to be used in a disposable garment without tearing when subjected to the stresses of wear; and at least one break-away panel comprised of one or more strips of manually tearable material uninterruptedly extending from one leg opening to the waist opening so as to provide a zone which can be torn apart so the disposable undergarment can be easily removed from the wearer. A preferred embodiment may comprise two break-away panels, one extending from each leg opening to the waist opening; an absorbent member attached to the inner surface of the disposable undergarment to absorb and contain exudates discharged from the body; and elasticized legbands and waistbands substantially surrounding the leg openings and waist opening respectively, so the disposable undergarment will snugly fit its wearer.

BRIEF DESCRIPTION OF THE DRAWINGS

While the specification concludes with claims particularly pointing out and distinctly claiming the subject matter which is regarded as forming the present invention, it is believed that the invention will be better understood from the following descriptions which are taken in conjunction with the accompanying drawings in which:

DETAILED DESCRIPTION OF THE INVENTION

Figure 1:
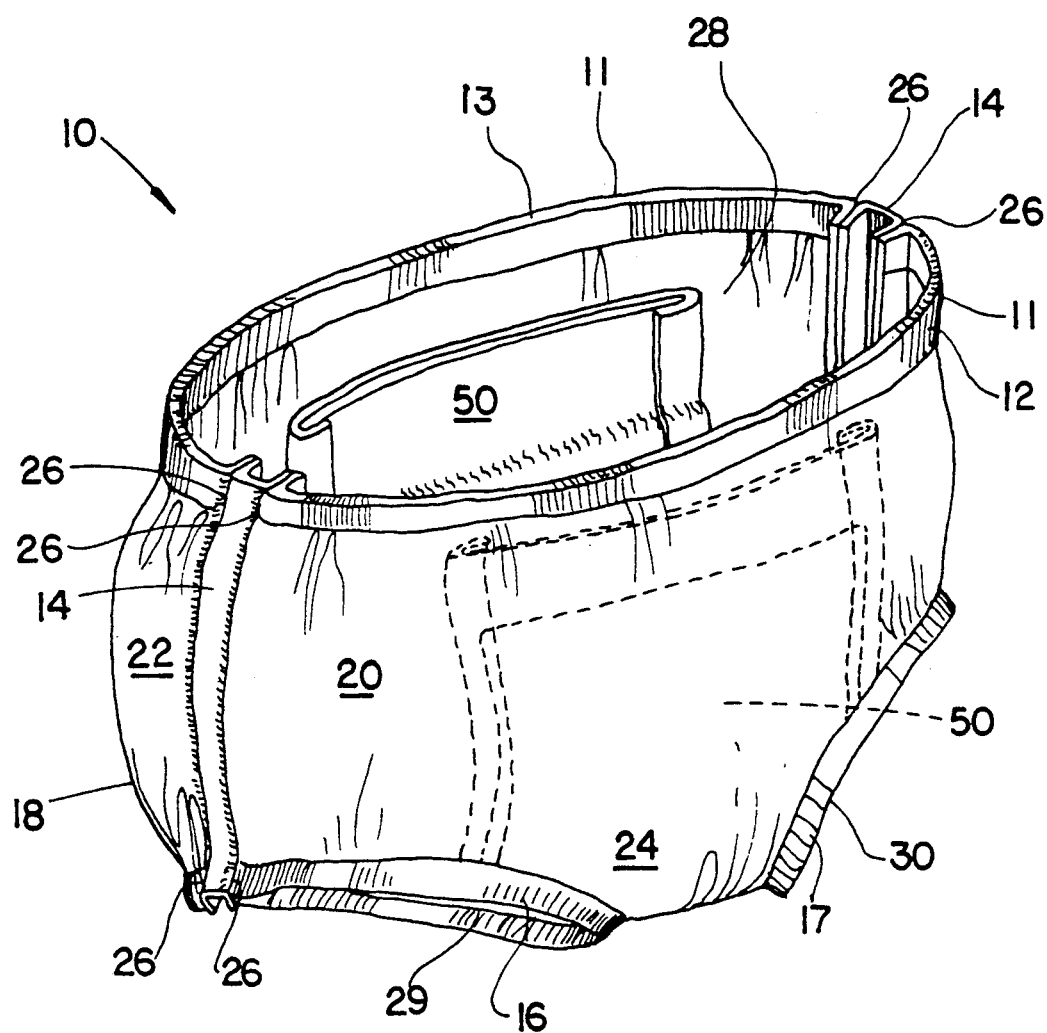
FIG. 1 is a perspective view of a preferred embodiment of the disposable undergarment of the present invention, disposable training pants.

As used herein, the term "disposable undergarment" refers to a garment worn next to the skin and usually under other clothing, which covers the lower torso and is intended to be discarded after a single use (i.e., it is not intended to be laundered or otherwise restored or reused). A preferred embodiment of the disposable undergarment of the present invention, disposable training pants 10, is shown in FIG. 1. As used herein, the term "disposable training pants" refers to disposable undergarments which absorb and contain body exudates and more specifically refers to disposable undergarments which comprise an absorbent means therein and are intended to be worn by a child while the child is being trained to control bladder and bowel movements and to use the toilet. It should be understood, however, that the present invention is also applicable to other disposable undergarments which may include incontinent briefs, disposable diapers, and the like.

Referring now to the drawings in detail wherein like reference numerals represent like parts throughout the several figures, FIG. 1 is a perspective view of the present invention in its preferred embodiment, a disposable training pant 10. The disposable training pant 10 includes a front portion 20, a rear portion 22, and a crotch portion 24 which together make up the chassis 18 of the training pants 10. The break-away panels 14 are each connected to the front portion 20 and the rear portion 22 along seams 26, and extend uninterruptedly from right leg opening 29 and left leg opening 30 to the waist opening 28. The waist opening 28 of the training pant 10 is substantially surrounded by an elasticized waistband comprising front waistband 12 and rear waistband 13. Right leg opening 29 is substantially surrounded by an elasticized legband 16, and left leg opening 30 is substantially surrounded by elasticized legband 17. The disposable training pant 10 has disposed on the inner surface of the chassis 18 an absorbent member 50 which will be described in greater detail herein below.

Though it is preferable that the chassis 18 should perform the dual functionality of providing moisture imperviousness and also providing a textile feel and look for the training pant 10, the chassis 18 of training pants 10 may be fabricated from a cotton or paper-like substance or any appropriate material that will provide the desired comfort, strength and appearance. Therefore the chassis 18 can be made of a carded, spunbond or spunlace nonwoven web of synthetic fibers such as polypropylene, polyethylene or polyester fibers; a nonwoven web of cellulosic fibers, textile fibers such as rayon fibers, cotton and the like, or a blend of cellulosic and textile fibers; a nonwoven web of synthetic fibers such as polypropylene, polyethylene or polyester fibers mixed with cellulosic, pulp fibers or textile fibers; or melt blown thermoplastic fibers, such as macrofibers or microfibers, of polypropylene, polyethylene, polyester or other thermoplastic materials or mixtures of such thermoplastic macrofibers or microfibers with cellulosic, pulp or textile fibers The chassis 18 can also be a laminated structure of a nonwoven material with a waterproofing coating such as a polyethylene film. It is preferable, however, to use a hydrophobic polypropylene spunbond fabric that has a nearly uniform fiber dispersion so that the tensile strengths are similar in both the machine direction and cross direction of the fabric. If nonwoven material of that type is not available, another nonwoven material which will work well is a hydrophobic polypropylene carded fabric. Nonwoven material of this type is commercially available through suppliers such as Fiberweb North America of Simpsonville, S.C. or Veratech of Walpole, Mass. and is marketed in the trade as carded hydrophobic polypropylene thermally bonded nonwoven.

The disposable training pant 10 has two break-away panels 14 uninterruptedly extending from each leg opening, right leg opening 29 and left leg opening 30, to the waist opening 28. The break-away panels 14 allow the training pants 10 to be easily removed from the user by pulling the front portion 20 and the rear portion 22 of the training pants 10 which will cause the break-away panel 14 to tear along its length, opening the sides of training pant 10 between the waist opening 28 and the right leg opening 29 on the right side of the training pant 10 and between the waist opening 28 and the left leg opening 30 on the left side of the training pant 10. The break-away panel 14 may be fabricated from a single layer or multiple layers of a cotton or paper-like substance or any appropriate manually tearable material that will provide the desired comfort, strength and appearance. Preferably it is one or more layers of a hydrophobic, nonwoven material such as the materials which comprise the chassis 18. The tensile strength of the break-away panel 14 should be great enough to withstand forces during wear, and weak enough to be broken by manual tearing. The tensile strength of break-away panel 14 should also be less than the tensile strength of the seams 26 on each side of the break-away panel 14. Preferably the tensile strength of the break-away panel 14 is less than or equal to the tensile strength of the chassis material. As positioned in the training pants 10, its cross-directional (CD) tensile strength should be in the range of 500 to 5,000 grams/inch, more preferably in the range of 2,000 to 3,000 grams/inch.

The tensile strength is measured using a universal constant rate of elongation tensile testing instrument with light duty flat face jaws, such as the Instron 1101-TN, 1102-TNS, 1122 or 1130, Instron Engineering Corporation, Canton Mass., or Thwing-Albert Intellect 500, Thwing-Albert Instrument Company, 10960 Dutton Road, Philadelphia, Pa. 19154 or equivalent.

The tensile tester is a device constructed in such a way that a gradually increasing load is smoothly applied to a defined sample portion until the sample portion fails. The tensile at the point of failure is frequently called "peak" tensile, or just "peak." The results reported are generally the average load in grams of force at peak.

Prior to testing the tensile tester should be calibrated and zeroed according to the manufacturer's instructions and a load cell should be chosen such that the tensile results for the strips tested will be between 25% and 75% of the capacity of the load cell or load range used. The material to be sampled should be conditioned for at least two hours in a room maintained at 73° F.±2° F. (22.8°C.±1.12° C.) and 50% relative humidity ±2%. The material to be sampled should be folded in such a way that strips can be cut 3 plys deep. The strips should be 1 inch by about 7 to 10 inches and should be cut using a JDC double edge cutter, available from Thwing-Albert Instrument Company. At least three test strips should be prepared for each sample for each sample direction, i.e. machine direction or cross direction. The instrument crosshead should be set to operate at 5 inches/minute, and the gauge length should be set at 5 inches. If the tensile tester uses a strip chart recorder, set the chart speed for 5 inches/minute for machine direction (MD) testing and 2 inches/minute for cross direction (CD) testing. For instruments not employing a chart recorder, but presenting data in a digital display format on a panel meter, prepare the instrument microprocessor (Intellect 500) or microcon (Instron) following the manufacturer's instructions as required for the test being performed.

Insert one sample strip only into the top clamp. Align the strip between the top and bottom clamp and clamp the strip into the bottom clamp with enough tension to eliminate any slack in the sample. Keep handling of tensile strips to a minimum. When inserting strips, take care to touch the portions of the strips that will be between the jaws only when necessary. When the sample is properly clamped in the tester, it will not be loose, or slack, between the jaws, and neither will it be too taught. Any cockles (wrinkles) or waviness in the sample should be removed, or better, use a different sample strip. Start the crosshead moving downward. If a recorder is used, it must be started exactly at the instant the tensile test begins, or be recording prior to the beginning of the test. At the moment the pin reaches its highest peak on the chart, quickly read or stop the top integrator counter switch if a separate integrator is being used. Allow the test to continue until the pin returns completely to zero on the chart. When the pin reaches zero on the chart, stop the bottom integrator counter if a separate integrator is being used. Determine the integrator readings for peak work and total work, if integrators are being used or determine peak and total energy values following the manufacturer's instructions for the readout device used. Return the crosshead to its original starting position, turn off the recorder if one is being used and remove the torn strips from both jaws. Repeat the test for the remaining two strips.

Tensile values for machine direction or cross direction are individually calculated based upon peak load values determined for at least three test strips of each sample in the machine direction (MD) or cross direction (CD).

Average Tensile (gm/in) =

$$\frac{\text{Sum of Peak Loads for Samples Tested}}{\text{Number of Test Strips Tested}}$$

Calculate and report to the nearest whole unit.

Since the size of disposable undergarment varies to accommodate wearers ranging from infants to adults, the size of the break-away panel also varies. However, referring to the disposable training pant 10 represented in the drawings, the height, or length, of the break-away panel will vary according to its location in the training pant 10 and the distance between the waist opening 28 and the leg openings 29, 30; and the width of the panel as positioned in the training pant 10 will preferably range from about ⅛" to 3" (about 3 mm to 75 mm), and more preferably about ¼" to ¾" (about 6 mm to 20 mm). As used in an adult disposable undergarment, the height, or length, of the break-away panel again will vary according to the location of the break-away panel in the undergarment and the distance from the waist opening to the leg openings; the width of the break-away panel as positioned in the undergarment will preferably range from about ⅛" to 6" (about 3 mm to 150 mm), and more preferably about ¼" to 2" (about 6 mm to 50 mm).

Another method by which a suitable break-away panel (not shown) can be made is by securing in the disposable undergarment a strip of one or more layers of material folded or doubled over at its ends so as to form a break-away panel with increased mass and strength at its top and bottom. Referring to FIG. 1 the tops of the break-away panels 14 are those parts of the break-away panels 14 which are secured between the front waistband 12 and rear waistband 13, and which together with the front waistband 12 and rear waistband 13 form the waist opening 28. The bottom of the break-away panel is that part of the break away panel which is secured between the ends of one of the legbands and which together with that legband forms one of the leg openings. The advantage of this type of break-away panel is that it allows a weaker, less expensive material to be used for the break-away panel, while providing sufficient strength at the top and bottom of the break-away panel where the stresses are the greatest. The tensile strength at the top and bottom of the break-away panel 14 will typically be less than the tensile strength of the waistband and the legband due to the elastic materials and mass of these features. Thus, the legband and waistband increase the strength of the chassis adjacent the seams 16 so that the top or bottom of the tearaway panel will burst before the others. However, this type of break-away panel is not preferred.

Though the preferred embodiment of the disposable training pants 10 has a break-away panel 14 disposed on the sides of the disposable training pants 10, it should be understood that the break-away panel may be located more towards the front of the disposable training pant 10 or more towards the rear of the disposable training pant 10 so long as the break-away panel extends from the waist opening to a leg opening and provides a region which is substantially free from additional thickness or mass, such as absorbent material or plastic waistbands or legbands, which could inhibit or hinder the tearing of the disposable training pant 10 because of higher tensile strengths. It should also be understood that the invention may comprise one break-away panel or more than one break-away panel.

Figure 2:
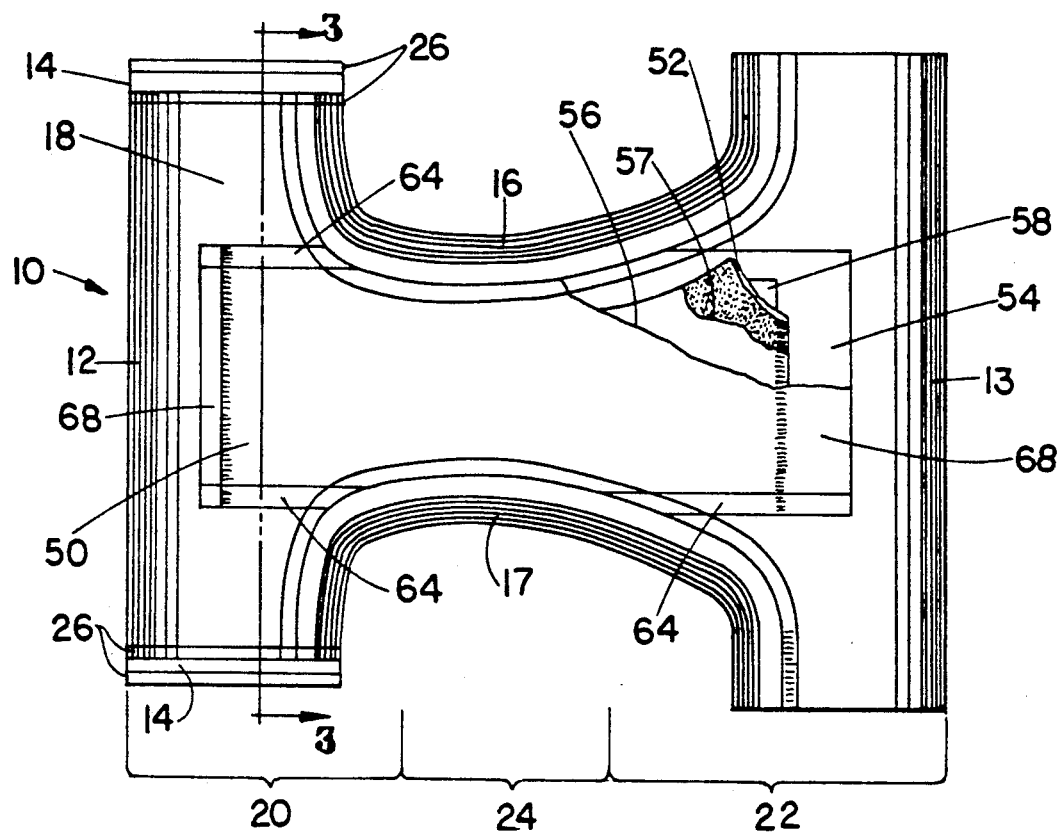
FIG. 2 is a partially cut-away plan view of the training pants of FIG. 1 laid out flat for illustrative purposes.

The waistband of the disposable undergarment is that portion of the disposable undergarment which is intended to be placed adjacent to the wearer's waist. The disposable training pant 10 of the present invention is preferably constructed so as to have two waistbands, a front waistband 12 and and a rear waistband 13, as can be seen in FIG. 1 and FIG. 2. While the disposable undergarments may be constructed so as to have a single unitary waistband encircling the waist of the wearer, such a design is not preferred because it would interfere with the operation of the break-away panel. It is also possible to construct a disposable undergarment having three or more waistband sections, but these embodiments, too, are not preferred. Although the waistbands may be extensions of the chassis of the disposable undergarment, the waistbands preferably comprise separate elements affixed to the chassis of the disposable undergarment.

A disposable undergarment may comprise one or more elastically contractible waistbands. There are many well known methods used to make elastically contractible waistbands, such as securing an elastic element (e.g., one or more strips of ribbon or rope elastic) to the waistband material or between two or more layers of waistband material. The waistband preferably has the elastic element disposed throughout its entire length, though it may be disposed only through a portion of its length. However, the waistband should not hinder or inhibit the operation of the break-away panel. Referring to FIGS. 1 and 2, the present invention preferably comprises two elastically contractible waistbands, front waistband 12 and rear waistband 13, comprising five strands of rubber elastic glued between layers of hydrophobic spunbond nonwoven material. Preferably the rear waistband 13 will have greater elastic force than that of the front waistband 12. And, rear waistband 13 will preferably have a force ranging from about 100 to 400 grams force at 85% extension and front waistband 12 will preferably have a force ranging from about 80 to 200 grams force at 85% extension to help keep the front waistband 12 from gradually falling below the stomach of the wearer. Commercially available elastic elements which have been found to work well in the front waistband 12 and rear waistband 13 are, respectively, Fulflex 6311 (0.017 inches×0.019 inches) and Fulflex 6511 0.023 inches×0.033 inches) sold through Fulflex, Inc., P.0. Box 4549, Middletown, R.I., 02840. An adhesive which has been found suitable for gluing the elastic elements to the waistbands is commercially available through Findley Adhesives of Wauwatoga, Wisc. and marketed as H-2085.

The legbands of the disposable undergarment are those portions of the disposable undergarment which are intended to be placed adjacent the wearer's legs. The legbands preferably comprise separate elements affixed to the chassis of the undergarment, however, they may be extensions of the chassis. Though disposable undergarments may be constructed with legbands which entirely encircle the leg of the wearer, such a design is not preferred because it would interfere with the operation of the break-away panel. The disposable undergarment preferably also comprises legbands which are elastically contractible. There are many well known methods used to make elastically contractible legbands, such as, for example, securing one or more strips of ribbon or rope elastic to the legband material or between two or more layers of legband material. The legband is preferably elasticized throughout its entire length, though it may be elasticized through only a portion of its length. However, the elasticized legband should not inhibit or hinder the operation of the break-away panel. Referring to FIGS. 1 and 2, the right legband 16 and left legband 17 preferably comprise layers of hydrophobic spunbond nonwoven material with five strands of rubber elastic glued throughout the entire length of the legband between the layers of nonwoven material. A commercially available elastic element which has been found to work well in the legbands 16, 17 is Fulflex 6311 0.017 inches×0.019 inches) sold through Fulflex, Inc., P.0. Box 4549, Middletown, R.I., 02840. An adhesive which has been found suitable for gluing the elastic elements to the waistbands is commercially available through Findley Adhesives of Wauwatoga, Wisc. and marketed as H-2085.

The elasticized waistbands 12 and 13, the break-away panel 14, and the elasticized legbands 16 and 17 can all be secured to the disposable training pant chassis 18 by any of several means which are well known in the art, such as thermal bonding, ultrasonic welding, pressure bonding or adhesive bonding. However, the preferable method is stitching because it provides a garment-line appearance to the disposable training pants 10. Lockstitching and backstitching as are known in the sewing art are preferably used, though there are many types of stitching which will also work well (e.g., overlock stitching).

The break-away panel 14 is joined to the chassis at seams 26 by any of several means which are well known in the art, such as thermal bonding, ultrasonic welding, pressure bonding or adhesive bonding. However, the preferable method is stitching because it provides a garment like appearance to the disposable training pant 10. Lockstitching and backstitching as are known in the sewing art are preferably used, though there are many types of stitching which will also work well (e.g., overlock stitching). The tensile strength of the seam 26 should be greater than the tensile strength of the breakaway panel 14 because of the increased mass at the seam 26 and/or the different materials used to create the seam 26. The legband and waistband material also add to the tensile strength of the chassis material adjacent the seam 26.

Figure 3:
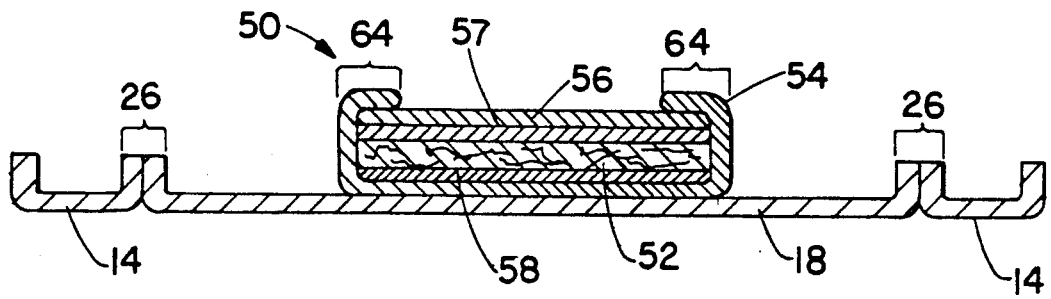
FIG. 3 is a sectional view of cross section 3—3 of FIG. 2.

Referring to FIG. 2 and FIG. 3, there is shown an absorbent member 50 which is attached to the inside surface of the chassis 18 and is provided to absorb and contain the various exudates discharged from the body. A suitable absorbent member 50 may be any of the absorbent means well known in the art that will provide the desired absorbent capacity for the training pants 10.

Examples of articles having suitable absorbent means are shown in Reissue U.S. Pat. No. 32,649 entitled "Hydrogel Forming Polymer Compositions For Use In Absorbent Structures" which issued to Kerryn A. Brandt, Steven A. Goldman, and Thomas A. England on Apr. 19, 1988; and U.S. Pat. No. 4,834,735 entitled "High Density Absorbent Members Having Low Density And Lower Basis Weight Acquisition Zones" which issued to Miguel Alemany and Charles J. Berg on May 30, 1989; which patents are incorporated herein by reference.

Though the absorbent member 50 may be assembled in a variety of well known configurations, a preferred configuration, shown in FIG. 3, comprises a topsheet 56, an absorbent core 52, a top tissue 57 disposed on the top surface of absorbent core 52, a bottom tissue 58 disposed on the bottom surface of absorbent core 52, and a liquid impermeable backsheet 54. The absorbent member 50 is also preferably thin so the disposable training pants resemble an undergarment rather than a bulky disposable diaper.

The topsheet 56 should be compliant, soft feeling, and nonirritating to the wearer's skin. Further, the topsheet 56 is liquid pervious permitting liquids to readily penetrate through its thickness. A suitable topsheet 56 may be manufactured from a wide range of materials such as porous foams, reticulated foams, apertured plastic films, natural fibers (e.g., wood or cotton fibers), synthetic fibers (e.g., polyester or polypropylene fibers) or from a combination of natural and synthetic fibers. Preferably, the topsheet 56 is made of a hydrophillic material comprising about 25% to 35% rayon so as to feel wet and signal a discharge of urine to a toilet training child.

A particularly preferred topsheet material is manufactured by Fiberweb North America and marketed in the trade as 75/25 polypropylene/rayon carded thermally bonded nonwoven.

The absorbent core 52 may be any means which is generally compressible, conformable, nonirritating to the wearer's skin, and capable of absorbing and retaining liquids and certain body exudates.

The absorbent core 52 may be manufactured in a wide variety of sizes and shapes and from a wide variety of liquid absorbent materials commonly used in disposable diapers and other absorbent articles, such as comminuted wood pulp which is generally referred to as airfelt. Examples of other suitable absorbent materials include creped cellulose wadding, absorbent foams, absorbent sponges, super absorbent polymers, absorbent gelling materials, or any equivalent materials or combination of materials. The total absorbent capacity of the absorbent core 52 should, however, be compatible with the designed exudate loading and the intended use of the disposable training pant 10. Further, the size and absorbent capacity of the absorbent core 52 may be varied to accommodate wearers ranging from infants through adults.

An exemplary embodiment of the absorbent core 52 comprises a layer of absorbent material comprising hydrophillic fibers and particles of absorbent gelling material (hydrogel) such as the absorbent structure described in U.S. Pat. No. 4,610,678 entitled "High Density Absorbent Structure" which issued to Paul T. Weisman and Steven A. Goldman on Sept. 9, 1986, and the disclosure of which is incorporated herein by reference. An alternative embodiment of the absorbent core 52 is a dual layered absorbent core in a preferred configuration such as is generally described in U.S. Pat. No. 4,673,402 entitled "Absorbent Article with Dual Layered Cores" which issued to Paul T. Weisman, Dawn I. Houghton and Dale A. Gellert on June 16, 1987, and the disclosure of which is incorporated herein by reference, having an asymmetric shaped upper layer and a lower layer. A particularly preferred embodiment of an absorbent core 52 useful in the present invention is described in U.S. Pat. No. 4,834,735 entitled "High Density Absorbent Members Having Lower Density and Lower Basis Weight Acquisition Zones" which issued to Miguel Alemany and Charles J. Berg on May 30, 1989, which discloses absorbent members having a storage zone and an acquisition zone having a lower average density and a lower average basis weight per unit area than the storage zone so that the acquisition zone may effectively and efficiently rapidly acquire discharged liquid. The disclosure of this U.S. Patent is hereby incorporated herein by reference.

A preferred embodiment of the absorbent member 50 has a modified hourglass-shaped absorbent core 52. It should be understood, however, that the size, shape, configuration and total absorbent capacity of the absorbent core 52 may be varied to accommodate wearers ranging from infants to adults. Therefore, the dimensions, shape and configuration of the absorbent core 52 may be varied (e.g., the absorbent core 52 may have a varying caliper, or a hydrophillic radiant, or may or may not contain absorbent gelling materials). The absorbent core 52 is preferably a batt of airfelt and particles of absorbent gelling material, about 15 centimeters wide (lateral dimension), about 34 centimeters long (longitudinal dimension) and approximately 7 centimeters across the narrowest part of the crotch portion 24.

The top tissue 57 and bottom tissue 58 are substantially the same and are disposed on opposite sides of the absorbent core 52. The top tissue and bottom tissue 57, 58 may be any type of hydrophillic nonwoven material, such as those well known in the art, which will lend support to the absorbent core 52 and keep absorbent gelling material from falling out of the absorbent core 52. A suitable tissue material is commercially available from Georgia Pacific and is marketed in the trade as "absorbent tissue".

As used herein, the term "absorbent structure" refers collectively to the topsheet 56, the top tissue 57, the bottom tissue 58, and the absorbent core 52, with the core 52 being disposed between the top tissue 57 and the bottom tissue 58, and the top tissue 57 being disposed between the topsheet 56 and the absorbent core 52, as seen in FIG. 3. The topsheet 56 will preferably be the same length as the backsheet 54 (FIG. 2) and will extend, in the longitudinal direction, beyond the absorbent core 52, the top tissue 57, and the bottom tissue 58.

The absorbent structure has attachment means (not shown) between the topsheet 56 and the top tissue 57, between the top tissue 57 and the absorbent core 52, and between the absorbent core 52 and the bottom tissue 58. Though the attachment means (not shown) may be any of those well known in the art, such as a continuous layer of adhesive, a patterned layer of adhesive, or an array of separate line or spots of adhesive, the attachment means is preferably a spray adhesive. Suitable adhesives are available commercially through Findley Adhesives of Wauwatoga, Wisc. and marketed in the trade as 990-374C.

The backsheet 54 is positioned adjacent the absorbent structure. The backsheet 54 is preferably impervious to liquids and is preferably manufactured from a thin plastic film, although other liquid impervious materials may also be used. The backsheet 54 prevents the exudates absorbed and contained in the absorbent structure from wetting articles which contact the disposable training pants such as outer clothing and bedsheets. Preferably, the backsheet 54 is a polyethylene film having a thickness from about 0.8 millimeters to about 1.2 millimeters, although other flexible, liquid impervious materials may be used. As used herein, the term "flexible" refers to materials which are compliant and which will readily conform to the general shape and contours of the human body. Suitable polyethylene films are manufactured by Exxon Chemical Americas of Lake Zurich, Ill. and marketed in the trade as ENB570. The backsheet 54 may permit vapors to escape from the absorbent structure while still preventing exudates from passing through the backsheet 54.

The backsheet 54 is attached to the absorbent structure by an attachment means (not shown). The attachment means may be any of those well known in the art. For example, the backsheet 54 may be secured to the absorbent structure by a uniform continuous layer of adhesive, a patterned layer of adhesive, or an array of separate lines or spots of adhesive. Preferably spiral gluing is used for the attachment means, though spray gluing and other attachment means well known in the art may also be used. Adhesives which have been found to be satisfactory are manufactured by Findley Adhesives of Wauwatoga, Wisc. and marketed in the trade as H2031.

The size of the backsheet 54 is dictated by the size of the wearer and the exact absorbent member design selected. In the preferred embodiment of FIGS. 2 and 3, the backsheet 54 has a modified hourglass shape extending beyond the absorbent structure, wraps up and over the longitudinal edges of the absorbent structure and is attached to the longitudinal edges of the topsheet 56 to provide a barrier to wicking 64. Barrier to wicking 64 preferably exists only in the front portion 20 and rear portion 22 and not in the crotch portion 24. The preferred embodiment of the absorbent member 50 will also have a barrier to wicking 68, in the front portion 20 and rear portion 22 where the topsheet 56 and backsheet 54 extend longitudinally beyond the absorbent core 52 and the top and bottom tissue 57, 58; the topsheet 56 is placed adjacent the backsheet 54 and is preferably attached (not shown) thereto using the spiral gluing referred to herein above, although spray gluing and other attachment means well known in the art may also be used. The barriers to wicking 64, 68 are provided to prevent body exudates from wicking into the disposable training pant chassis 18.

The absorbent member 50 is positioned adjacent the inside surface of the training panty chassis 18 and is attached thereto by attachment means (not shown). The attachment means may be any of those well known in the art. For example, the absorbent member 50 may be secured to the training pants chassis 18 by a uniform continuous layer of adhesive, a patterned layer of adhesive or an array of separate lines or spots of adhesive. Preferably the entire back of the absorbent insert 50 is glued to the inside of the training pant chassis 18 by means of spiral gluing, though spray gluing and other attachment means well known in the art may also be used. Adhesives which have been found to be satisfactory are manufactured by Findley Adhesives of Wauwatoga, Wisc. and marketed in the trade as H2031.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A disposable undergarment comprising a chassis having a front portion, a rear portion, and a crotch portion joining said front portion and said rear portion, said chassis comprising substantially throughout the front portion, rear portion and crotch portion a material which is suitable to be used in a disposable garment without tearing when subjected to the stresses of wear, said front portion and said rear portion being secured so as to form a waist opening and two leg openings, said leg openings being separated by said crotch portion; and at least one breakaway panel which comprises one or more strips of manually tearable material uninterruptedly extending from one said leg opening to said waist opening, so as to provide a zone in which the garment can be torn apart for easier removal from the user, said breakaway panel being joined to said chassis at a first seam and a second seam, the tensile strength of said breakaway panel being less than the tensile strength of said first seam and less than the tensile strength of said second seam.

2. The disposable undergarment of claim 1, wherein two breakaway panels are used; one of said breakaway panels uninterruptedly extending from one leg opening to the waist opening, the other said breakaway panel uninterruptedly extending from the other leg opening to the waist opening, so as to allow the garment to be torn open at said breakaway panels and removed from the user without sliding the garment over one or both legs of the user.

3. The disposable undergarment of claim 1, wherein said leg openings comprise an elastic expansion and contraction medium disposed in at least the crotch portion to form legbands so as to allow the leg openings to accommodate legs of various girths.

4. The disposable undergarment of claim 1, wherein an elastic expansion and contraction medium is disposed along at least the rear portion of said waist opening to form a rear waistband.

5. The disposable undergarment of claim 4, wherein said elastic expansion and contraction medium has a force ranging from about 100 to about 400 grams force at 85% extension.

6. The disposable undergarment of claim 1, wherein an elastic expansion and contraction medium is disposed along at least the front portion of said waist opening to form a front waistband.

7. The disposable undergarment of claim 6, wherein said elastic expansion and contraction medium has a force ranging from about 80 to about 200 grams force at 85% extension.

8. The disposable undergarment of claim wherein said disposable undergarment further comprises an absorbent member secured to at least a portion of the inside surface of said chassis of the undergarment, so as to allow the undergarment to be utilized by a person who is incontinent or being toilet trained.

9. The disposable undergarment of claim 8, wherein said absorbent member comprises an absorbent core.

10. The disposable undergarment of claim 9, wherein said absorbent core comprises a blend of about 60–95% airfelt and about 5–40% absorbent gelling material.

11. The disposable undergarment of claim 9, wherein said absorbent member comprises a hydrophillic topsheet.

12. The disposable undergarment of claim 11, wherein said hydrophillic topsheet comprises about 25–35% rayon.

13. The disposable undergarment of claim 8, wherein said absorbent member comprises a hydrophobic backsheet.

14. The undergarment of claim 13, wherein said hydrophobic backsheet wraps up along the longitudinal edges of said absorbent member so as to provide a barrier to wicking of urine.

15. The undergarment of claim 14, wherein said barrier to wicking exists only on that part of said absorbent member which is away from said crotch portion.

16. The disposable undergarment of claim 8, wherein said absorbent member comprises a hydrophillic top tissue and a hydrophillic bottom tissue.

17. The disposable undergarment of claim 16, wherein said absorbent core is disposed between said top tissue and said bottom tissue.

18. The undergarment of claim 8, wherein the entire backsheet of said absorbent member is glued to the inside of said chassis of the undergarment.

19. The undergarment of claim 8, wherein the backsheet of said absorbent member is partially glued to the inside of said chassis of the disposable undergarment.

20. The disposable undergarment of claim 1, wherein said first seam and said second seam are formed by means of stitching.

21. The disposable undergarment of claim 20, wherein said stitching comprises lockstitching and backstitching.

22. The disposable undergarment of claim 20, wherein said stitching comprises overlock stitching.

23. The disposable undergarment of claim 1, wherein said first seam and said second seam are formed by ultrasonic bonding.

24. The disposable undergarment of claim 1, wherein said first seam and said second seam are formed by heat sealing.

25. The disposable undergarment of claim 1, wherein said first seam and said second seam are formed by pressure sealing.

26. The disposable undergarment of claim 1, wherein said first seam and said second seam are formed by adhesive bonding.

27. The disposable undergarment of claim 1, wherein said breakaway panel is made of a nonwoven material having a cross-directional tensile strength between 500 and 5,000 grams/inch.

28. The disposable undergarment of claim wherein said breakaway panel is made of a nonwoven material having a cross-directional tensile strength between 2,000 and 3,000 grams/inch.

29. The disposable undergarment of claim 1, wherein said chassis comprises substantially throughout said front portion, said rear portion and said crotch portion a hydrophobic spunbond, carded or spunlace nonwoven material comprising polypropylene, polyester or polyethylene fibers.

* * * * *

UNITED STATES PATENT AND TRADEMARK OFFICE
CERTIFICATE OF CORRECTION

PATENT NO. : 5,074,854
DATED : December 24, 1991
INVENTOR(S) : Karen M. Davis

It is certified that error appears in the above-identified patent and that said Letters Patent is hereby corrected as shown below:

Column 2, Line 23, "portion, o and" should read ---portion, and---.

Column 3, Line 24, "waistband comprising" should read ---waistband 11 comprising---.

Column 3, Line 50, "fibers The" should read ---fibers. The---.

Column 6, Line 26, "or plastic" should read ---or elastic---.

Column 7, Line 43, "6311 0.017" should read ---6311 (0.017---.

Column 10, Line 20, "pants such" should read ---pants 10 such---.

Column 12, Line 7, "claim wherein" should read ---Claim 1, wherein---.

Column 13, Line 3, "claim wherein" should read ---Claim 1, wherein---.

Signed and Sealed this

Twenty-seventh Day of April, 1993

Attest:

MICHAEL K. KIRK

*Attesting Officer*  *Acting Commissioner of Patents and Trademarks*